(12) United States Patent
Williams et al.

(10) Patent No.: US 11,904,119 B2
(45) Date of Patent: *Feb. 20, 2024

(54) BALLOON CATHETER

(71) Applicant: ABBOTT CARDIOVASCULAR SYSTEMS INC., Santa Clara, CA (US)

(72) Inventors: Kerry J. Williams, Temecula, CA (US); George Doratt, Corona, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/573,213

(22) Filed: Jan. 11, 2022

(65) Prior Publication Data

US 2022/0280758 A1 Sep. 8, 2022

Related U.S. Application Data

(63) Continuation of application No. 16/580,636, filed on Sep. 24, 2019, now Pat. No. 11,253,681, which is a
(Continued)

(51) Int. Cl.
*A61M 25/10* (2013.01)
*A61M 25/00* (2006.01)
(Continued)

(52) U.S. Cl.
CPC ............. *A61M 25/10* (2013.01); *A61L 29/06* (2013.01); *A61L 29/148* (2013.01);
(Continued)

(58) Field of Classification Search
CPC .............. A61M 25/10; A61M 25/1034; A61M 25/1036; A61B 2017/00526
See application file for complete search history.

(56) References Cited

U.S. PATENT DOCUMENTS

| 4,522,867 A | 6/1985 | Hill, Jr. et al. |
| 4,771,778 A * | 9/1988 | Mar ..................... A61M 25/104 604/103.1 |

(Continued)

FOREIGN PATENT DOCUMENTS

| EP | 1 084 728 A1 | 3/2001 |
| EP | 1 306 062 A1 | 5/2003 |

(Continued)

OTHER PUBLICATIONS

U.S. Appl. No. 13/481,441 (now U.S. Pat. No. 8,834,510), filed May 25, 2012 (Sep. 16, 2014).
(Continued)

*Primary Examiner* — Courtney B Fredrickson
(74) *Attorney, Agent, or Firm* — Baker Botts L.L.P.

(57) ABSTRACT

Balloon catheter includes an outer shaft having a hypotube and a monolithic single-layer distal outer member, a balloon in fluid communication with an inflation lumen, and a monolithic inner tubular member having a guidewire lumen defined therethrough. The outer shaft has the inflation lumen defined therethrough. The monolithic single-layer distal outer member is necked to a reduced diameter along an entire length thereof. A proximal end of the monolithic single-layer distal outer member is coupled to the hypotube. A distal section of the hypotube comprises a skive defined by a first angled cut, an axial cut, and a second angled cut. The balloon has a proximal balloon shaft coupled to a distal end of the monolithic single-layer distal outer member. The monolithic inner tubular member extends distally from a proximal port in the monolithic single-layer distal outer member through the balloon to form a tip.

8 Claims, 7 Drawing Sheets

Related U.S. Application Data continuation of application No. 14/843,372, filed on Sep. 2, 2015, now Pat. No. 10,426,934.

(60) Provisional application No. 62/163,839, filed on May 19, 2015, provisional application No. 62/046,157, filed on Sep. 4, 2014.

(51) Int. Cl.
| | | |
|---|---|---|
| *A61L 29/06* | (2006.01) | |
| *A61L 29/14* | (2006.01) | |
| *A61M 25/01* | (2006.01) | |
| *A61B 17/00* | (2006.01) | |

(52) U.S. Cl.
CPC .... *A61M 25/0009* (2013.01); *A61M 25/0052* (2013.01); *A61M 25/104* (2013.01); *A61M 25/1034* (2013.01); *A61M 25/1036* (2013.01); *A61B 2017/00526* (2013.01); *A61M 2025/0183* (2013.01)

(56) References Cited

U.S. PATENT DOCUMENTS

| | | | |
|---|---|---|---|
| 4,782,834 A | 11/1988 | Maguire et al. | |
| 4,976,690 A | 12/1990 | Solar et al. | |
| 5,156,594 A | 10/1992 | Keith | |
| 5,217,434 A | 6/1993 | Arney | |
| 5,217,482 A | 6/1993 | Keith | |
| 5,279,562 A | 1/1994 | Sirhan et al. | |
| 5,370,616 A | 12/1994 | Keith et al. | |
| 5,370,655 A | 12/1994 | Burns | |
| 5,387,193 A | 2/1995 | Miraki | |
| 5,387,225 A | 2/1995 | Euteneuer et al. | |
| 5,395,334 A | 3/1995 | Keith et al. | |
| 5,423,754 A | 6/1995 | Cornelius et al. | |
| 5,458,615 A | 10/1995 | Klemm et al. | |
| 5,490,837 A | 2/1996 | Blaeser et al. | |
| 5,507,768 A | 4/1996 | Lau et al. | |
| 5,522,818 A | 6/1996 | Keith et al. | |
| 5,533,968 A | 7/1996 | Muni et al. | |
| 5,643,209 A | 7/1997 | Fugoso et al. | |
| 5,649,909 A | 7/1997 | Cornelius | |
| 5,743,875 A | 4/1998 | Sirhan et al. | |
| 5,833,706 A | 11/1998 | St. Germain et al. | |
| 5,908,406 A | 6/1999 | Ostapchenko et al. | |
| 6,083,232 A | 7/2000 | Cox | |
| 6,102,890 A | 8/2000 | Stivland et al. | |
| 6,217,547 B1* | 4/2001 | Lee | A61L 29/049 604/103 |
| 6,277,093 B1 | 8/2001 | Lee | |
| 6,575,958 B1 | 6/2003 | Happ et al. | |
| 6,595,958 B1 | 7/2003 | Mickley | |
| 6,620,127 B2 | 9/2003 | Lee et al. | |
| 6,695,812 B2 | 2/2004 | Estrada et al. | |
| 6,702,802 B1 | 3/2004 | Hancock et al. | |
| 6,746,423 B1 | 6/2004 | Wantink | |
| 6,863,678 B2 | 3/2005 | Lee et al. | |
| 6,887,219 B2 | 5/2005 | Wantink | |
| 6,890,318 B2 | 5/2005 | Wantink | |
| 6,923,822 B2 | 8/2005 | Crawford et al. | |
| 6,964,750 B2 | 11/2005 | Fulford | |
| 7,001,420 B2 | 2/2006 | Speck et al. | |
| 7,074,206 B2 | 7/2006 | Lee et al. | |
| 7,195,611 B1 | 3/2007 | Simpson et al. | |
| 7,273,470 B2 | 9/2007 | Wantink | |
| 7,303,798 B2 | 12/2007 | Bavaro et al. | |
| 7,322,959 B2 | 1/2008 | Warnack et al. | |
| 7,549,975 B2 | 6/2009 | Lee et al. | |
| 7,828,766 B2 | 11/2010 | Durcan | |
| 7,833,597 B2 | 11/2010 | Bavaro et al. | |
| 7,862,541 B2 | 1/2011 | Jeffrey et al. | |
| 7,906,066 B2 | 3/2011 | Wilson et al. | |
| 7,951,259 B2 | 5/2011 | Duchamp et al. | |
| 7,967,781 B2 | 6/2011 | Simpson et al. | |
| 7,967,836 B2 | 6/2011 | Warnack et al. | |
| 8,048,058 B2 | 11/2011 | Fulford | |
| 8,052,638 B2 | 11/2011 | Lee et al. | |
| 8,057,430 B2 | 11/2011 | Grovender et al. | |
| 8,251,949 B2 | 8/2012 | Warnack | |
| 8,382,738 B2 | 2/2013 | Simpson et al. | |
| 8,382,935 B2 | 2/2013 | Simpson et al. | |
| 8,394,055 B2 | 3/2013 | Durcan | |
| 8,444,608 B2 | 5/2013 | Haslinger et al. | |
| 8,444,802 B2 | 5/2013 | Lee et al. | |
| 8,637,132 B2 | 1/2014 | Bavaro et al. | |
| 8,834,510 B2 | 9/2014 | Wilson et al. | |
| 8,840,743 B2 | 9/2014 | Wantink et al. | |
| 9,132,259 B2 | 9/2015 | Lin et al. | |
| 2002/0072705 A1 | 6/2002 | Vrba et al. | |
| 2002/0146557 A1 | 10/2002 | Claude et al. | |
| 2003/0125709 A1 | 7/2003 | Eidenschink | |
| 2003/0135231 A1 | 7/2003 | Goodin et al. | |
| 2004/0073250 A1* | 4/2004 | Pederson, Jr. | A61F 2/958 606/192 |
| 2004/0082935 A1 | 4/2004 | Lee et al. | |
| 2004/0256049 A1* | 12/2004 | O'Shaughnessy | B29C 65/02 156/158 |
| 2005/0070847 A1 | 3/2005 | van Erp et al. | |
| 2005/0261725 A1 | 11/2005 | Crawford et al. | |
| 2006/0135909 A1 | 6/2006 | Holman et al. | |
| 2007/0021772 A1 | 1/2007 | Von Oepen et al. | |
| 2007/0173919 A1 | 7/2007 | Maschke | |
| 2008/0015499 A1 | 1/2008 | Warnack | |
| 2008/0077085 A1 | 3/2008 | Eidenschink et al. | |
| 2008/0125707 A1 | 5/2008 | Wilson et al. | |
| 2009/0036829 A1 | 2/2009 | Pagel et al. | |
| 2009/0171281 A1 | 7/2009 | Pipenhagen et al. | |
| 2009/0223624 A1 | 9/2009 | Lee et al. | |
| 2010/0130925 A1 | 5/2010 | Haslinger et al. | |
| 2010/0189876 A1 | 7/2010 | Kokish et al. | |
| 2010/0217234 A1 | 8/2010 | Grovender | |
| 2010/0285085 A1 | 11/2010 | Stankus et al. | |
| 2011/0022150 A1 | 1/2011 | Durcan | |
| 2011/0060276 A1 | 3/2011 | Schaeffer et al. | |
| 2011/0070355 A1 | 3/2011 | Bavaro et al. | |
| 2011/0160834 A1 | 6/2011 | Aggerholm | |
| 2011/0172696 A1 | 7/2011 | Jeffrey et al. | |
| 2012/0065718 A1 | 3/2012 | Simpson et al. | |
| 2012/0226229 A1 | 9/2012 | Watanabe et al. | |
| 2012/0302952 A1 | 11/2012 | Kitada et al. | |
| 2012/0302994 A1 | 11/2012 | Wilson et al. | |
| 2012/0303054 A1 | 11/2012 | Wilson et al. | |
| 2013/0178795 A1 | 7/2013 | Wilson et al. | |
| 2014/0276401 A1 | 9/2014 | Lee et al. | |
| 2015/0367554 A1* | 12/2015 | Klausen | B29C 49/4278 264/165 |

FOREIGN PATENT DOCUMENTS

| | | |
|---|---|---|
| JP | 2001-333984 A | 12/2001 |
| JP | 2008-237844 A | 10/2008 |
| JP | 2010-220760 A | 10/2010 |
| JP | 2014-519865 A | 8/2014 |
| JP | 2016-055165 A | 4/2016 |
| JP | 6-114109 B2 | 4/2017 |
| WO | WO 01/43944 A1 | 6/2001 |
| WO | WO 03/037418 A2 | 5/2003 |
| WO | WO 2008/005706 A2 | 1/2008 |
| WO | WO 2012/042619 A1 | 4/2012 |
| WO | WO 2012/162651 A1 | 11/2012 |

OTHER PUBLICATIONS

U.S. Appl. No. 14/458,327 (now U.S. Pat. No. 9,616,198), filed Aug. 13, 2014 (Apr. 11, 2017).

U.S. Appl. No. 14/843,074 (now U.S. Pat. No. 10,426,933), filed Sep. 2, 2015 (Oct. 1, 2019).

U.S. Appl. No. 14/843,249 (now U.S. Pat. No. 10,086,175), filed Sep. 2, 2015 (Oct. 2, 2018).

U.S. Appl. No. 14/843,308 (now U.S. Pat. No. 10,406,318), filed Sep. 2, 2015 (Sep. 10, 2019).

(56) References Cited

OTHER PUBLICATIONS

U.S. Appl. No. 14/843,372 (now U.S. Pat. No. 10,426,934), filed Sep. 2, 2015 (Oct. 1, 2019).
U.S. Appl. No. 15/449,462 (now U.S. Pat. No. 10,449,339), filed Mar. 3, 2017 (Oct. 22, 2019).
U.S. Appl. No. 16/580,636 (now U.S. Pat. No. 11,253,681), filed Sep. 24, 2019 (Feb. 22, 2022).
U.S. Appl. No. 13/481,441, dated Aug. 13, 2014 Issue Fee payment.
U.S. Appl. No. 13/481,441, dated Jun. 18, 2014 Notice of Allowance.
U.S. Appl. No. 13/481,441, dated Apr. 18, 2014 Response to Non-Final Office Action.
U.S. Appl. No. 13/481,441, dated Dec. 18, 2013 Non-Final Office Action.
U.S. Appl. No. 13/481,441, dated Sep. 12, 2013 Response to Restriction Requirement.
U.S. Appl. No. 13/481,441, dated Aug. 15, 2013 Restriction Requirement.
U.S. Appl. No. 14/458,327, dated Mar. 3, 2017 Issue Fee Payment.
U.S. Appl. No. 14/458,327, dated Dec. 5, 2016 Notice of Allowance.
U.S. Appl. No. 14/458,327, dated Nov. 14, 2016 Response to Restriction Requirement.
U.S. Appl. No. 14/458,327, dated Sep. 13, 2016 Restriction Requirement.
U.S. Appl. No. 14/843,074, dated Aug. 20, 2019 Issue Fee Payment.
U.S. Appl. No. 14/843,074, dated Aug. 5, 2019 Notice of Allowance.
U.S. Appl. No. 14/843,074, dated May 28, 2019 Notice of Allowance.
U.S. Appl. No. 14/843,074, dated Apr. 10, 2019 Response to Non-Final Office Action.
U.S. Appl. No. 14/843,074, dated Mar. 21, 2019 Applicant Initiated Interview Summary.
U.S. Appl. No. 14/843,074, dated Jan. 10, 2019 Non-Final Office Action.
U.S. Appl. No. 14/843,074, dated May 22, 2018 Amendment and Request for Continued Examination (RCE).
U.S. Appl. No. 14/843,074, dated May 15, 2018 Applicant Initiated Interview Summary.
U.S. Appl. No. 14/843,074, dated Nov. 22, 2017 Final Office Action.
U.S. Appl. No. 14/843,074, dated Oct. 5, 2017 Response to Non-Final Office Action.
U.S. Appl. No. 14/843,074, dated Jun. 5, 2017 Non-Final Office Action.
U.S. Appl. No. 14/843,249, dated Aug. 28, 2018 Issue Fee Payment.
U.S. Appl. No. 14/843,249, dated May 31, 2018 Notice of Allowance.
U.S. Appl. No. 14/843,249, dated May 18, 2018 Applicant Initiated Interview Summary.
U.S. Appl. No. 14/843,249, dated May 8, 2018 Response after Final Action.
U.S. Appl. No. 14/843,249, dated Nov. 21, 2017 Final Office Action.
U.S. Appl. No. 14/843,249, dated Oct. 12, 2017 Response to Non-Final Office Action.
U.S. Appl. No. 14/843,249, dated Jul. 12, 2017 Non-Final Office Action.
U.S. Appl. No. 14/843,308, dated Jul. 19, 2019 Issue Fee Payment.
U.S. Appl. No. 14/843,308, dated May 22, 2019 Notice of Allowance.
U.S. Appl. No. 14/843,308, dated Mar. 21, 2019 Applicant Initiated Interview Summary.
U.S. Appl. No. 14/843,308, dated Mar. 13, 2019 Response to Non-Final Office Action.
U.S. Appl. No. 14/843,308, dated Dec. 13, 2018 Non-Final Office Action.
U.S. Appl. No. 14/843,308, dated May 17, 2018 Amendment and Request for Continued Examination (RCE).
U.S. Appl. No. 14/843,308, dated May 15, 2018 Applicant Initiated Interview Summary.
U.S. Appl. No. 14/843,308, dated May 1, 2018 Advisory Action.
U.S. Appl. No. 14/843,308, dated Apr. 12, 2018 Response after Final Action.
U.S. Appl. No. 14/843,308, dated Nov. 17, 2017 Final Office Action.
U.S. Appl. No. 14/843,308, dated Aug. 4, 2017 Response to Non-Final Office Action.
U.S. Appl. No. 14/843,308, dated Apr. 4, 2017 Non-Final Office Action.
U.S. Appl. No. 14/843,372, dated Sep. 4, 2019 Notice of Allowance.
U.S. Appl. No. 14/843,372, dated Aug. 22, 2019 Issue Fee Payment.
U.S. Appl. No. 14/843,372, dated May 22, 2019 Notice of Allowance.
U.S. Appl. No. 14/843,372, dated Mar. 21, 2019 Applicant Initiated Interview Summary.
U.S. Appl. No. 14/843,372, dated Mar. 13, 2019 Response to Non-Final Office Action.
U.S. Appl. No. 14/843,372, dated Dec. 13, 2018 Non-Final Office Action.
U.S. Appl. No. 14/843,372, dated May 21, 2018 Amendment and Request for Continued Examination (RCE).
U.S. Appl. No. 14/843,372, dated May 16, 2018 Applicant Initiated Interview Summary.
U.S. Appl. No. 14/843,372, dated Nov. 21, 2017 Final Office Action.
U.S. Appl. No. 14/843,372, dated Aug. 4, 2017 Response to Non-Final Office Action.
U.S. Appl. No. 14/843,372, dated Apr. 4, 2017 Non-Final Office Action.
U.S. Appl. No. 15/449,462, dated Sep. 13, 2019 Issue Fee Payment.
U.S. Appl. No. 15/449,462, dated Sep. 13, 2019 Notice of Allowance.
U.S. Appl. No. 15/449,462, dated Jun. 18, 2019 Notice of Allowance.
U.S. Appl. No. 16/580,636, dated Jan. 11, 2022 Issue Fee Payment.
U.S. Appl. No. 16/580,636, dated Oct. 12, 2021 Notice of Allowance.
U.S. Appl. No. 16/580,636, dated Sep. 28, 2021 Terminal Disclaimer Filed.
European Search Report dated Jan. 29, 2016 in EP Application No. 15183531.
European Search Report dated Oct. 13, 2016 in Application No. EP 15183533.
European Search Report dated Oct. 14, 2016 in Application No. EP 15183534.
International Search Report for PCT/US2012/039678, dated Sep. 21, 2012 (Corresponds to U.S. Appl. No. 13/481,441).
Partial European Search Report dated Jan. 29, 2016 in EP Application No. 15183539.

* cited by examiner

BALLOON CATHETER

REFERENCE TO RELATED APPLICATIONS

This application is a continuation of U.S. patent application Ser. No. 16/580,636, filed Sep. 24, 2019, which is a continuation of U.S. patent application Ser. No. 14/843,372, filed Sep. 2, 2015, now U.S. Pat. No. 10,426,934, which claims priority to U.S. Provisional Patent Application No. 62/046,157, filed Sep. 4, 2014, and U.S. Provisional Patent Application No. 62/163,839, filed May 19, 2015, the content of each of which is hereby incorporated by reference in its entirety.

BACKGROUND

Field of the Disclosed Subject Matter

The disclosed subject matter relates to medical devices, for example to balloon catheters for use in angioplasty and/or stent or scaffold delivery.

Description of Related Art

In percutaneous transluminal coronary angioplasty (PTCA) procedures, a guiding catheter is advanced in the vasculature of a patient until the distal tip of the guiding catheter is seated in a desired coronary artery. A guidewire is advanced out of the distal end of the guiding catheter into the coronary artery until the distal end of the guidewire crosses a lesion to be dilated. A dilatation catheter, having an inflatable balloon on the distal portion thereof, is advanced into the coronary anatomy over the previously introduced guidewire until the balloon of the dilatation catheter is positioned across the lesion. Once positioned, the dilatation balloon is inflated with inflation fluid one or more times to a predetermined size at a suitable pressure to compress the stenosis against the arterial wall to open up the vascular passageway. Generally, the inflated diameter of the balloon is approximately the same diameter as the native diameter of the body lumen being dilated to complete the dilatation but not over expand the artery wall. After the balloon is deflated, blood resumes flowing through the dilated artery and the dilatation catheter and the guidewire can be removed therefrom.

In such angioplasty procedures, there may be restenosis of the artery, i.e., reformation of the arterial blockage, which necessitates either another angioplasty procedure, or some other method of repairing or strengthening the dilated area. To reduce the restenosis rate and to strengthen the dilated area, physicians may additionally or alternatively implant an intravascular prosthesis inside the artery at the site of the lesion. Such stents or scaffolds may be bare metal, polymeric, or coated with a drug or other therapeutic agent. Stents or scaffolds may also be used to repair vessels having an intimal flap or dissection or to generally strengthen a weakened section of a vessel. Stents or scaffolds are usually delivered to a desired location within a coronary artery in a contracted condition on a balloon of a catheter which is similar in many respects to a balloon angioplasty catheter and expanded to a larger diameter by expansion of the balloon. The balloon is deflated to remove the catheter with the stent implanted within the artery at the site of the dilated lesion. Coverings on an inner or an outer surface of the stent have been used in, for example, the treatment of pseudoaneurysms and perforated arteries, and to prevent prolapse of plaque. Similarly, vascular grafts comprising cylindrical tubes made from tissue or synthetic materials such as polyester, expanded polytetrafluoroethylene, and DACRON® may be implanted in vessels to strengthen or repair the vessel, or used in an anastomosis procedure to connect vessels segments together. For details of example stents, see for example, U.S. Pat. No. 5,507,768 to Lau, et al. and U.S. Pat. No. 5,458,615 to Klemm, et al., the contents of each of which are incorporated herein by reference in their entireties.

In addition to percutaneous transluminal angioplasty (PTA), PTCA, and atherectomy procedures, balloon catheters are also used to treat the peripheral system such as in the veins system or the like. For instance, a balloon catheter is initially advanced over a guidewire to position the balloon adjacent a stenotic lesion. Once in place, the balloon is then inflated, and the restriction of the vessel is opened, and a stent or scaffold can be delivered if desired. Likewise, balloon catheters are also used for treatment of other luminal systems throughout the body.

Typically, balloon catheters comprise a hollow catheter shaft with a balloon secured at a distal end. The interior of the balloon is in a fluid flow relation with an inflation lumen extending along a length of the shaft. Fluid under pressure can thereby be supplied to the interior of the balloon through the inflation lumen. To position the balloon at the stenosed region, the catheter shaft is designed in multiple parts to have suitable pushability (i.e., the ability to transmit force along the length of the catheter), trackability, and flexibility, to be readily advanceable within the tortuous anatomy of the vasculature. The catheter is also designed so that it can be withdrawn from the patient after delivery. Conventional balloon catheters for intravascular procedures, such as angioplasty and stent delivery, frequently have a relatively stiff proximal shaft section to facilitate advancement of the catheter within the body lumen, a mid-shaft section of an intermediate (or transition) flexibility, and a relatively flexible distal shaft section to facilitate passage through tortuous anatomy, such as distal coronary and neurological arteries, without damage to the vessel wall or damage to the stent, in the case of stent delivery.

Traditional catheter shafts are often constructed with inner and outer member tubing with an annular space therebetween for balloon inflation. In the design of catheter shafts, it is desirable to predetermine or control characteristics such as strength, stiffness and flexibility of various sections of the catheter shaft to provide desired catheter performance. This is conventionally performed by combining separate lengths of tubular members of different material and/or dimensions and then assembling the separate members into a single shaft length. However, the transition between sections of different stiffness or material can be a cause of undesirable kinking along the length of the catheter. Such kinking is particularly evident in rapid exchange (RX) catheters, wherein the proximal shaft section does not include the additional structure of a guidewire lumen tube. For example, a conventional RX catheter generally consists of a proximal hypotube having a single inflation lumen therethrough, a mid-shaft transition section, and a dual lumen or coaxial tube configuration at a distal end section having both a guidewire lumen and an inflation lumen therein. Known techniques to minimize kinking at the transition between the more rigid proximal section and the more flexible distal section include bonding two or more segments of materials having different flexibility together to form the shaft. Such transition bonds need to be sufficiently strong to withstand the pulling and pushing forces on the shaft during use.

To address the described issues, catheters having varied flexibility and/or stiffness have been developed with various sections of the catheter shaft that are specifically tailored to provide desired catheter performance. For example, each of U.S. Pat. No. 4,782,834 to Maguire and U.S. Pat. No. 5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; U.S. Pat. No. 5,649,909 to Cornelius discloses a catheter having a proximal portion with greater stiffness due to the application of a polymeric coating thereto; and U.S. Pat. No. 8,444,608 to Haslinger discloses a multilayer catheter shaft using a combination of a high Shore D durometer value material and a lower Shore D durometer value material to reduce kinking, the contents of each of which are incorporated herein by reference in their entireties.

However, one difficulty has been balancing the often competing characteristics of strength and flexibility of the catheter shaft. In addition, use of multiple shaft sections can be a cause of undesirable kinking along the length of the catheter, and the bonds between the sections can be a location of failure (e.g., rupture) if any defects in the bonds exist.

As such, there remains a need for a catheter having a shaft with an improved combination of characteristics such as strength, flexibility, ease of manufacture, and lower cost. There is also a need for a catheter that has improved trackability to facilitate further passage through tortuous anatomy, such as distal coronary arteries, while maintaining the ability to withdraw from the tortuous anatomy without failure.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes balloon catheters and methods of making a balloon catheter. An exemplary balloon catheter includes an outer shaft including a hypotube and a monolithic single-layer distal outer member. The outer shaft has an inflation lumen defined therethrough. The monolithic single-layer distal outer member is necked to a reduced diameter along an entire length thereof, and a proximal end of the monolithic single-layer distal outer member is coupled to the hypotube. A distal section of the hypotube comprises a skive defined by a first angled cut, an axial cut, and a second angled cut. The balloon catheter also includes a balloon in fluid communication with the inflation lumen. The balloon has a proximal balloon shaft coupled to a distal end of the monolithic single-layer distal outer member. The balloon catheter also includes a monolithic inner tubular member having a guidewire lumen defined therethrough. The monolithic inner tubular member extends distally from a proximal port in the monolithic single-layer distal outer member through the balloon to form a tip.

In some embodiments, the balloon further comprises a distal balloon shaft having an inner diameter. The distal balloon shaft can have a distal seal portion coupled to the monolithic inner tubular member and a proximal portion free of attachment to the monolithic inner tubular member. The length of the proximal portion of the distal balloon shaft can be at least about two times the inner diameter of the distal balloon shaft.

In some embodiments, the monolithic single-layer distal outer member comprises polyether block amide. The polyether block amide can have a Shore durometer hardness of about 63D to about 72D, for example about 72D.

In some embodiments, the reduced diameter comprises a first reduced outer diameter and a first reduced inner diameter along a proximal portion of the monolithic single-layer distal outer member and a second reduced outer diameter and a second reduced inner diameter along the distal end of the monolithic single-layer distal outer member. The first reduced outer diameter can be about 0.038 inches to about 0.039 inches, the first reduced inner diameter can be about 0.029 inches to about 0.0295 inches, the second reduced outer diameter can be about 0.034 inches to about 0.035 inches, and the second reduced inner diameter can be about 0.029 inches to about 0.0295 inches. The length of the distal end of the monolithic single-layer distal outer member is about 1.0 mm to about 1.2 mm.

In some embodiments, the first angled cut of the skive can have a length of about 100 mm, the axial cut can have a length of about 25 mm, and the second angled cut can have a length of about 25 mm. The axial cut can have a height of about 0.0065 inches to about 0.0075 inches. The second angled cut can define a distal edge height of about 0.0035 inches to about 0.0045 inches. A proximal section of the hypotube can have an outer diameter of about 0.0275 inches to about 0.0285 inches and an inner diameter of about 0.0195 inches to about 0.0205 inches.

In some embodiments, a scaffold is mounted on the balloon. The scaffold can be bioresorbable.

According to another aspect of the disclosed subject matter, methods of making a balloon catheter are provided. An exemplary method includes necking a tubular member to form a monolithic single-layer distal outer member necked along an entire length thereof, providing a hypotube, coupling a proximal end of the monolithic single-layer distal outer member to the hypotube to form an outer shaft having an inflation lumen defined therethrough, and providing a balloon in fluid communication with the inflation lumen. The balloon has a proximal balloon shaft. The method also includes coupling the proximal balloon shaft to a distal end of the monolithic single-layer distal outer member and providing a monolithic inner tubular member having a guidewire lumen defined therethrough. The monolithic inner tubular member extends distally from a proximal port in the monolithic single-layer distal outer member through the balloon to form a tip.

In some embodiments, the balloon further comprises a distal balloon shaft having an inner diameter. The method can include coupling a distal seal portion of the distal balloon shaft to the monolithic inner tubular member and allowing a proximal portion of the distal balloon shaft to be free of attachment to the monolithic inner tubular member. The length of the proximal portion of the distal balloon shaft can be at least about two times the inner diameter of the distal balloon shaft.

In some embodiments, the tubular member is necked from a first outer diameter of about 0.045 inches to a first reduced outer diameter of about 0.038 inches to about 0.039 inches and from a first inner diameter of about 0.033 inches to a first reduced inner diameter of about 0.029 inches to about 0.0295 inches along a proximal portion of the monolithic single-layer distal outer member. The tubular member can be necked from a first outer diameter of about 0.045 inches to a second reduced outer diameter of about 0.034 inches to about 0.035 inches and from a first inner diameter of about 0.033 inches to a second reduced inner diameter of about 0.029 inches to about 0.0295 inches along the distal end of the monolithic single-layer distal outer member. The length of the distal end of the monolithic single-layer distal outer member can be about 1.0 mm to about 1.2 mm.

In some embodiments, the method can also include mounting a bioresorbable scaffold on the balloon and/or any of the features described herein above for the balloon catheter.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

DESCRIPTION

Reference will now be made in detail to the various exemplary embodiments of the disclosed subject matter, exemplary embodiments of which are illustrated in the accompanying drawings. The structure and method of making the disclosed subject matter will be described in conjunction with the detailed description of the balloon catheter.

In accordance the disclosed subject matter, a balloon catheter is provided. The balloon catheter includes an outer shaft including a hypotube and a monolithic single-layer distal outer member. The outer shaft has an inflation lumen defined therethrough. The monolithic single-layer distal outer member is necked to a reduced diameter along an entire length thereof, and a proximal end of the monolithic single-layer distal outer member is coupled to the hypotube. A distal section of the hypotube comprises a skive defined by a first angled cut, an axial cut, and a second angled cut. The balloon catheter also includes a balloon in fluid communication with the inflation lumen. The balloon has a proximal balloon shaft coupled to a distal end of the monolithic single-layer distal outer member. The balloon catheter also includes a monolithic inner tubular member having a guidewire lumen defined therethrough. The inner tubular member extends distally from a proximal port in the monolithic single-layer distal outer member through the balloon to form a tip.

The accompanying figures, where like reference numerals refer to identical or functionally similar elements throughout the separate views, serve to further illustrate various embodiments and to explain various principles and advantages all in accordance with the disclosed subject matter. For purpose of explanation and illustration, exemplary embodiments of the balloon catheter, and method of making thereof, in accordance with the disclosed subject matter are shown in FIGS. 1-12. While the present disclosed subject matter is described with respect to coronary indications, one skilled in the art will recognize that the disclosed subject matter is not limited to the illustrative embodiments, and that the product and methods described herein can be used in any suitable application.

Figures 1, 8, 9:
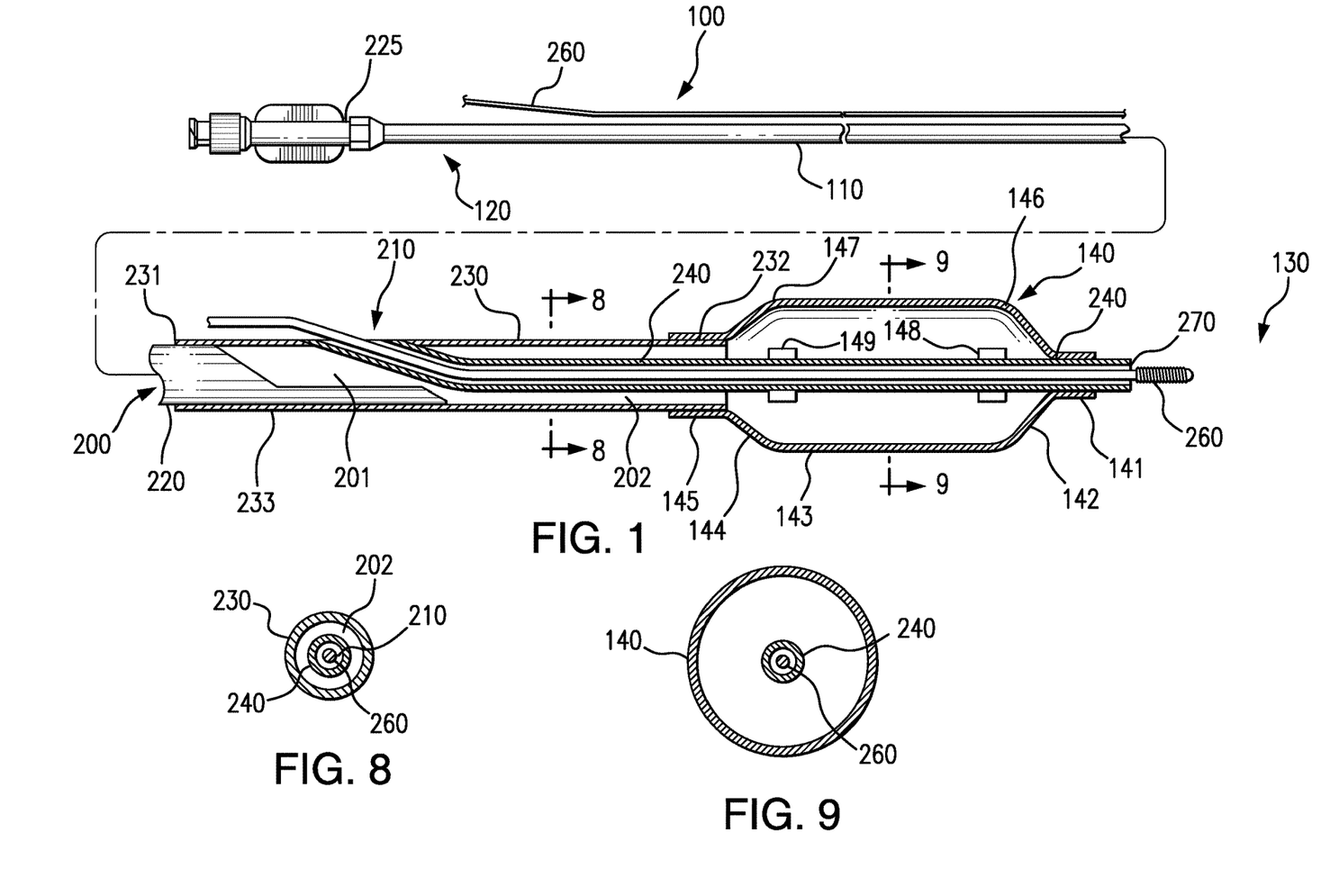
FIG. 1 is a side view, partially in section, of a balloon catheter embodying features of the disclosed subject matter.
FIGS. 8 and 9 are transverse cross sectional schematic views of the balloon catheter shown in FIG. 1, taken along lines 8-8 and 9-9, respectively.

For purpose of illustration, and not limitation, reference is made to an exemplary embodiment of a rapid exchange balloon dilatation catheter 100 shown in FIGS. 1-12. As shown in FIG. 1, the balloon catheter 100 generally comprises an elongated catheter shaft 110 having a proximal shaft section 120 and a distal shaft section 130. The catheter shaft 110 can have a variety of suitable configurations. For example, as illustrated in FIG. 1, an outer shaft of the elongate catheter shaft 110 can include a hypotube 220 and a monolithic single-layer distal outer member 230. The outer shaft including hypotube 220 and monolithic single-layer distal outer member 230 has an inflation lumen 200, 201, 202 defined therethrough, and the balloon catheter 100 includes a balloon 140 in fluid communication with the inflation lumen 200, 201, 202. The balloon catheter also includes a monolithic inner tubular member 240 having a guidewire lumen 210, 211 defined therethrough. The monolithic inner tubular member 240 extends distally from a proximal guidewire port 280 (shown FIG. 2) in the monolithic single-layer distal outer member 230 through the balloon 140 to from a tip 270.

Figure 2:
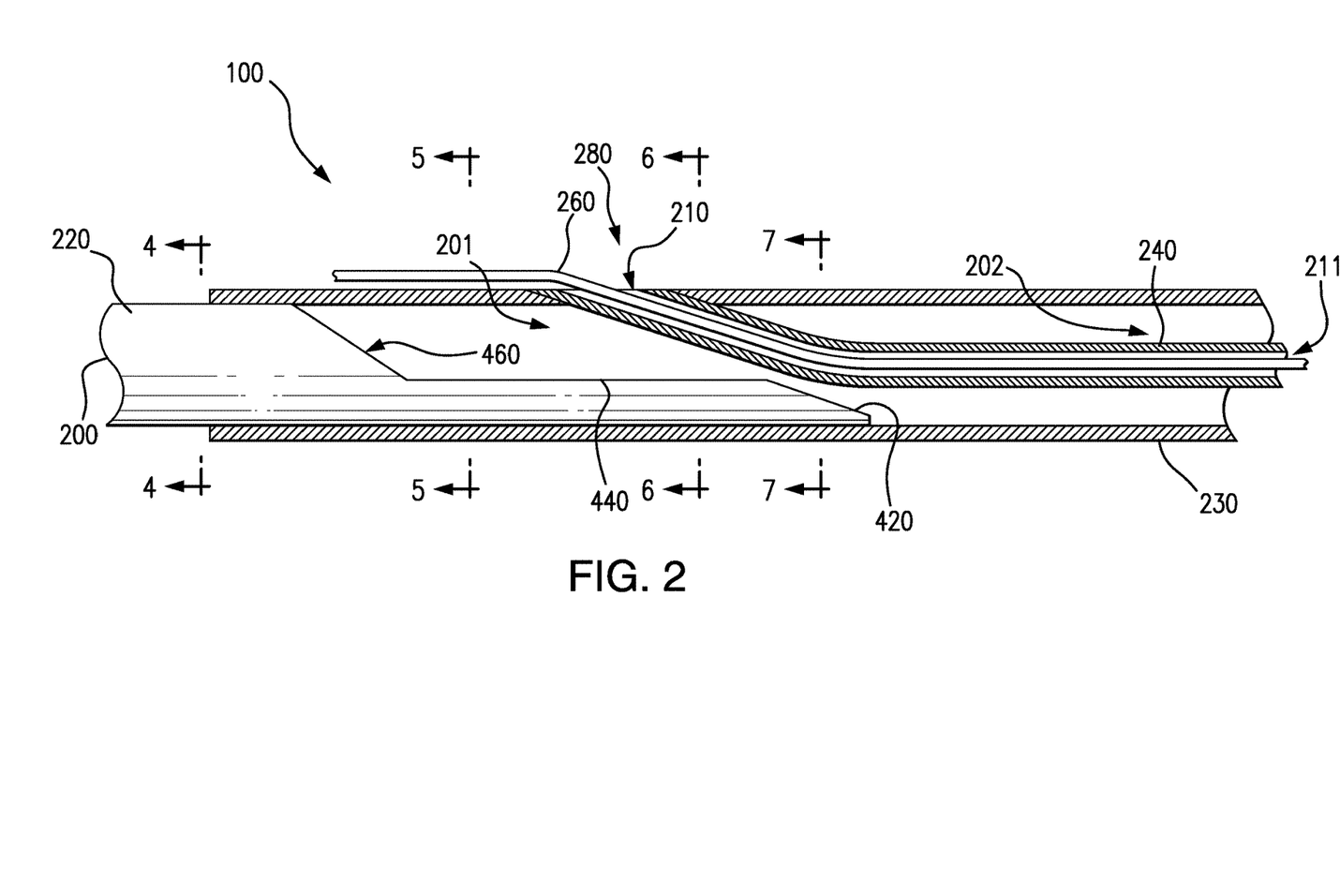
FIG. 2 is a detailed side cross section of the proximal port, including the skived distal end of the hypotube disposed within the inflation lumen of the distal outer member.

As depicted in FIGS. 1 and 2 for illustration, a proximal end 231 of the monolithic single-layer distal outer member 230 is coupled to the hypotube 220. The distal end 232 of the monolithic single-layer distal outer member 230 is coupled to a proximal balloon shaft 145 of the balloon 140 (as described below). Accordingly, the single-layer distal outer member 230 is a monolithic construction that extends distally from the hypotube 220 to the balloon 140. By contrast, typical balloon catheters include a separate midshaft portion bonded to the hypotube on one end and a separate distal outer shaft on the other end at a mid-lap seal. The monolithic construction of distal outer member 230, in accordance with the disclosed subject matter, thus provides a jointless outer member extending from the hypotube all the way to the proximal balloon seal and eliminates the mid lap-seal, which is one potential location of failure in known balloon catheters. The monolithic construction of distal outer member 230, in accordance with the disclosed subject matter, can provide a simpler design, easier and less expensive manufacturing, and less parts.

As embodied herein, the distal outer member 230 can comprise any suitable material. For example, the material can be a polyether block amide, commercially available under the trade name PEBAX®. The polyether block can have any suitable hardness, for example a Shore durometer hardness of about 63D to about 72D, preferably about 72D. Alternatively, nylons can be used alone or in combination (e.g., blended) with polyether block amide. While described herein as monolithic single layer distal outer member 230, alternatively a multilayer monolithic construction can be used. In one embodiment, a first layer can comprise polyether block amide and the second layer comprise nylon. Alternatively, first and second layers can both comprise polyether block amide or nylon.

Figure 11:
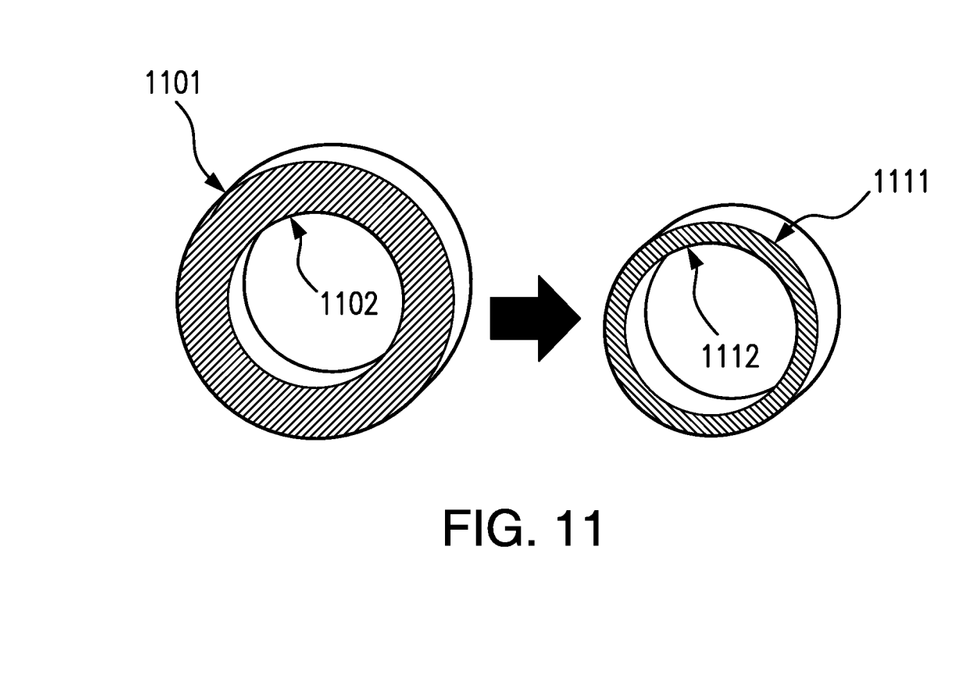
FIG. 11 is a partial cross-sectional view of an exemplary distal outer member prior to and after a necking process according to embodiments of the disclosed subject matter.

In accordance with the disclosed subject matter, the monolithic single-layer distal outer member 230 can be necked to a reduced diameter along an entire length thereof. In some embodiments, the distal outer member 230 can be necked by placing an extruded tube in a necking machine, as is known in the art. For example, the necking machine can use a heated die traversing along the length of the extruded tube having a mandrel therein to reduce the diameter of the distal outer member 230, as shown in FIG. 11 for the purpose of illustration and not limitation. The outer diameter of the tube can be controlled by the size of the die and the inner diameter of the tube can be controlled by the diameter of the mandrel. After necking, the necked tube can be stabilized at 125° C. for about 10 minutes.

In some embodiments, the diameter of the tube as extruded can be reduced from an outer diameter ("OD") of about 0.045 inch (1101 in FIG. 11) and an inner diameter ("ID") of about 0.033 inch (1102) to a reduced diameter of about 0.038 inch to about 0.039 inch OD (1111) and about 0.029 inch to about 0.0295 ID (1112) via necking. Thus, the double wall thickness of the necked tubing is about 0.01 inches. In some embodiments, the reduced diameter comprises a first reduced outer diameter and a first reduced inner diameter along a proximal portion 233 of the monolithic single-layer distal outer member and a second reduced outer diameter and a second reduced inner diameter along the distal end 232 of the monolithic single-layer distal outer member. For example, the first reduced outer diameter can be about 0.038 inches to about 0.039 inches, the first reduced inner diameter can be about 0.029 inches to about 0.0295 inches, the second reduced outer diameter can be about 0.034 inches to about 0.035 inches, and the second reduced inner diameter can be about 0.029 inches to about 0.0295 inches. The length of the distal end 232 of the monolithic single-layer distal outer member can be about 1.0 mm to about 1.2 mm.

In accordance with the disclosed subject matter, necking the distal outer member 230 can provide for more precise dimensions and decreased tolerances, can impart shear on the material, and can introduce partial orientation in the polymer material, which can increase the strength of the distal outer member without significantly effecting flexibility and provide for increased scaffold push. For example, it is desired for the rupture strength of the catheter shaft 110 to be greater than that of the balloon 140. As embodied herein, for example, the burst pressure of the necked distal outer member 230 can be significantly greater than (e.g., about 4 atm more than, or about 20% more than) that of the balloon 140. Also, introduction of partial (e.g., linear) orientation in the polymer material of the distal outer member can provide more column strength, more push, and can still allow for some play (e.g., stretching or elongating) during withdrawal from the tortuous anatomy and decrease the likelihood of rupture or separation as compared to a shaft made of a fully oriented polymer material (e.g., blown). Furthermore, having the distal end 232 of distal outer member 230 necked to a smaller diameter than the rest of the distal outer member 230 allows the proximal balloon shaft 145 to more easily fit over the distal outer member 230 for heat bonding to a reduce profile (as described below).

As embodied herein, the guidewire lumen 210, 211 can be defined by the monolithic inner tubular member 240 extending from the proximal port 280 through the monolithic single-layer distal outer member 230. The space between the monolithic single-layer distal outer member 230 and the monolithic inner tubular member 240 can define inflation lumen 202 in fluid communication with the inflation lumen 201. Thus, a coaxial annular configuration with the monolithic inner tubular member 240 positioned within the monolithic single-layer distal outer member 230 can be provided. Alternatively, the monolithic single-layer distal outer member 230 can be formed as a dual lumen member with the guidewire lumen and the inflation lumen defined therein.

For purpose of illustration and not limitation, FIG. 8 is a cross-section of the catheter 100 of FIG. 1 along the lines 8-8. As depicted in FIGS. 1 and 8, the inflation lumen 202 of the monolithic single-layer distal outer member 230 includes an annular configuration. The inflation lumen 202 is defined by the annular space between the interior surface of monolithic single-layer distal outer member 230 and the exterior surface of the monolithic inner tubular member 240, although a variety of suitable shaft configurations can alternatively be used including non-coaxial and multi-lumen extrusions. The transition from the circular to crescent to annular shape of the inflation lumens 200, 201, 202 allows for smooth flow without significant back pressure or resistance.

Figure 4:
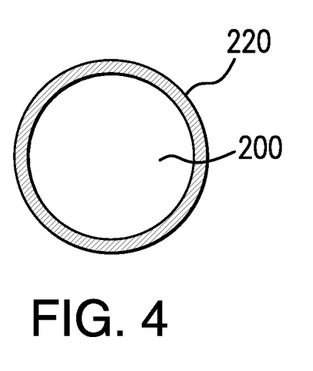
FIGS. 4, 5, 6, and 7 are transverse cross sectional schematic views of the balloon catheter shown in FIG. 2, taken along lines 4-4, 5-5, 6-6, and 7-7, respectively.

As embodied herein, the hypotube 220 can be a single lumen hypotube or similar tubular member of suitable rigidity and pushability. For example, the hypotube 220 can be a single piece construction tubular member. The hypotube 220 can have a proximal section 221 and a distal section 222 with an inflation lumen 200 and a longitudinal axis defined therethrough. The inflation lumen 200 of the hypotube 220 can comprise any suitable configuration, such as a substantially circular configuration as shown in FIG. 4.

In accordance with the disclosed subject matter, the distal section 222 of the hypotube 220 can comprise a skive, which is a cut section of the hypotube that gradually reduces in dimension distally along its length. For example, as illustrated in FIGS. 1 and 2, the hypotube 220 can be skived at its distal section 222 with a stepped configuration. The stepped skive in accordance with the disclosed subject matter can improve the pushability (e.g., push force transmission) and resistance to kinking (e.g., by reducing kink points) of the catheter by providing a smoother transition between the hypotube and the more distal catheter components (e.g., the monolithic single-layer distal outer member as further discussed herein). The stepped skive can also provide improved support for the proximal port 280 described herein.

Figure 3A:
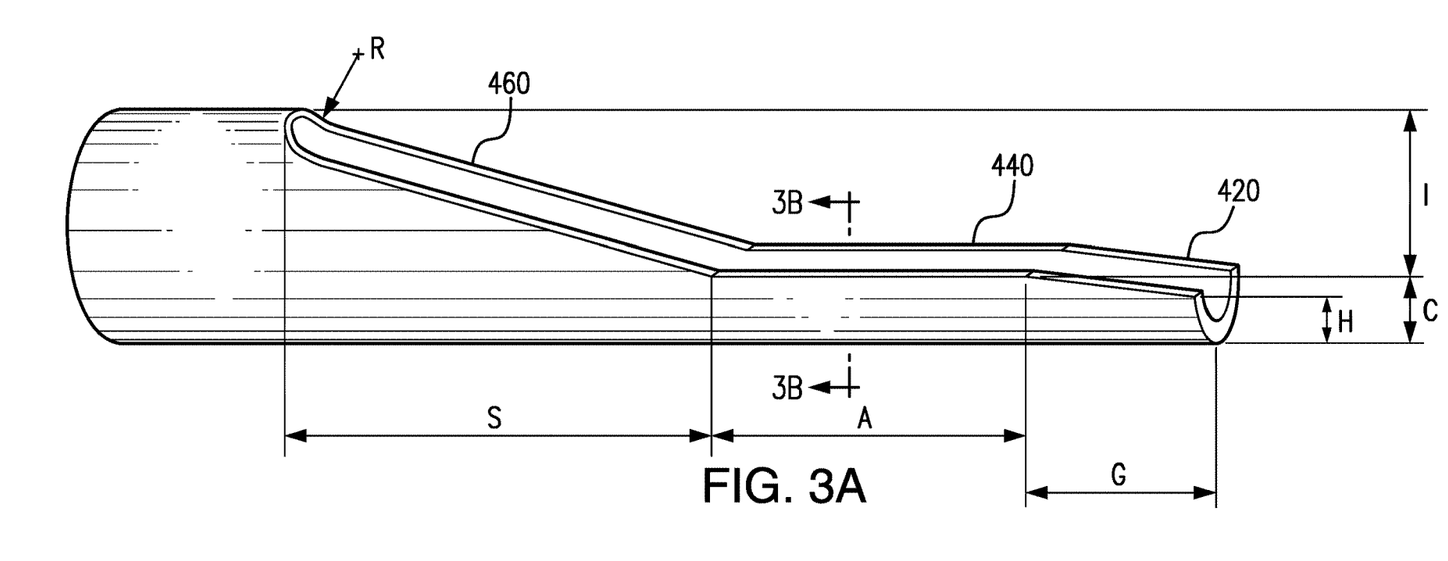
FIG. 3A is a detailed perspective view of the skive at the distal section of the hypotube according to embodiments of the disclosed subject matter.

In some embodiments of the disclosed subject matter, as depicted in FIG. 2, the skive of the hypotube 220 has three distinct sections including a first angled cut 420, an axial cut 440, and a second angled cut 460. The hypotube 220 can reduce in cross-sectional dimension distally along the length of the skive. The first angled cut 420 can be at the distal end of the hypotube 220 and the axial cut 440 can be disposed between the first angled cut 420 and the second angled cut 460 proximate the proximal end of the skive. The first angled cut 420 can come to a point at the extreme distal end of the skive/hypotube, as depicted in FIG. 2, or the distal end of the hypotube can include a blunt end as depicted in FIG. 3A. Other similar stepped configurations are contemplated.

In some embodiments, the first angled cut 420 and second angled cut 460 each can have a linear or straight angled configuration as depicted herein, or can be curved, such as a parabolic like curve. The first angled cut 420 and the second angled cut 460 can have the same angle of inclination or can have different angles of inclination. As depicted in FIG. 2, for purposes of illustration, the first angled cut 420 and the second angled cut 460 can be substantially parallel with each other. In other embodiments, the first angled cut 420 extends at a first angle relative the longitudinal axis of the hypotube 220 and the second angled 460 cut extends at a second angle relative the longitudinal axis of the hypotube 220 such that the first angle is different from the second angle. For example, but without limitation, angle 460 can be steeper than angle 420. In some embodiments, the angle for 420 is about 0.020° and the angle for 460 is approx. 0.3°. Preferably, the angles should be shallow (e.g., close to 0) to provide improved force transmission and reduce the chance of kinking.

Figure 3B:
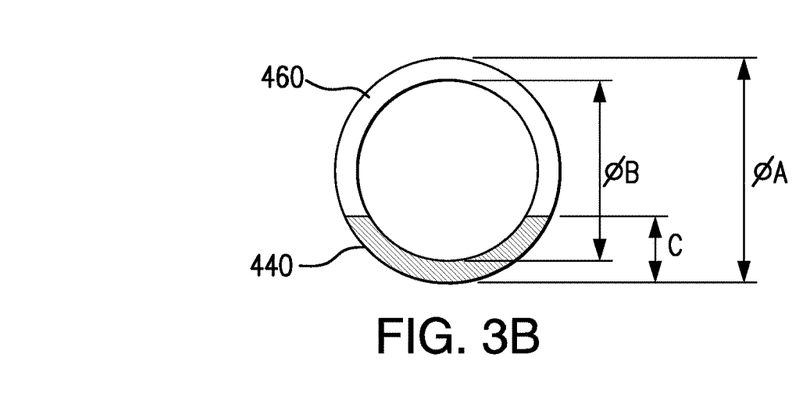
FIG. 3B is a cross section of the skive of the hypotube at section 3B-3B in FIG. 3A.

As embodied herein, the first angled cut 420, the axial cut 440, and the second angled cut 460 can have the same or varying lengths, although the overall dimensions can preferably correspond with dimensions of the monolithic single-layer distal outer member 230 as described further below. For the purpose of illustration, FIGS. 3A and 3B depict schematics of the distal section of the hypotube 220 for a coronary balloon dilation catheter, wherein the hypotube 220 has the first angled cut 420, the axial cut 440, and the second angled cut 460. In the example of FIGS. 3A and 3B, the first angled cut 420 has an axial length G between about 20 mm and about 30 mm, preferably about 25 mm plus or minus about 2 mm, for example about 25 mm. The first angled cut 420 of this embodiment has a blunt end which can have a distal height H ranging between about 5% to about 25% of the outer diameter of the hypotube 220. In some embodiments, the height H can be about 0.0025 inches to about 0.0065 inches, preferably about 0.0035 inches to about 0.0045 inches, for example about 0.0040 inches plus or minus 0.0005 inches.

As shown in FIG. 3A, the axial cut 440 can have an axial length A ranging between about 10 mm and about 40 mm, preferably about 25 mm plus or minus about 2 mm, for example about 25 mm. The axial cut 440 can have a height C, as depicted in FIG. 3A, that ranges between about 20% to about 50% of the outer diameter of the hypotube 220. For example, the height C ranges between about 0.0060 inches and about 0.0110 inches, preferably about 0.0065 inches to about 0.0075 inches.

For the purpose of illustration, FIG. 3B is a cross-section of FIG. 3A along the lines 3B-3B. FIG. 3B depicts the outside diameter OA and the inside diameter OB of the hypotube 220. In accordance with some embodiments of the disclosed subject matter, the skived hypotube 220 can have increased dimensions so as to form a thicker structure than previously described. For example, an increased thickness dimension can further improve column strength, push and kink resistance, and provide for enhanced scaffold control. For example, the inside diameter OB of the hypotube 220 can be about 0.0195 inches to about 0.0220 inches, preferably 0.0195 inches to about 0.0205 inches. The outside diameter OA of the hypotube 220 can be about 0.0260 inches to about 0.0285 inches, preferably about 0.0275 inches to about 0.0285 inches. The wall thickness of hypotube 220 can be between about 0.0030 inches and about 0.0090 inches, preferably about 0.0080 inches. FIG. 3B further depicts the height C of the axial cut 440 in relation to the outside diameter OA and the inside diameter OB.

As illustrated in FIG. 3A, the second angled cut 460 can have an overall height I when measured from a side of between about 50% to about 90% of the outer diameter of the hypotube 220, preferably about 85%. For example, the height I can about 0.021 inch for a 0.025 inch diameter hypotube. The second angled cut 460 can have a length S of about 95 mm to about 105 mm, preferably about 98 mm to about 102 mm, for example about 100 mm. FIG. 3B further depicts the height C of the axial cut 440 in relation to the outside diameter OA and the inside diameter OB.

Additionally, an end of one or more cuts can be radiused for transition purposes. For example, and as depicted in FIG. 3A, a proximal end of the second angled cut 460 can comprise a curved or radiused portion. The second angled cut 460 depicted herein includes a radius of approximately 0.040 inches plus or minus about 0.010 inches. In the embodiment of FIG. 3A, the overall axial length of the skive with respect to the first angled cut 420, the axial cut 440, and the second angled cut 460 can range from about 100 mm to about 200 mm. Additional suitable dimensions of the skive are contemplated. Additional features of a skived hypotube can be found in U.S. Patent Publication No. 2012/0303054, which is incorporated by reference herein in its entirety.

As depicted in FIG. 2 for purpose of illustration, the monolithic single-layer distal outer member 230 of the catheter 100 includes a guidewire lumen 210, 211 and an inflation lumen 201, 202 defined therethrough. The inflation lumen 201, 202 of the monolithic single-layer distal outer member 230 is in fluid communication with the inflation lumen 200 of the hypotube 220. Furthermore, at least a portion of the distal section of the hypotube 220 is disposed within the inflation lumen 201 of the monolithic single-layer distal outer member 230 with the inflation lumen 200 of the hypotube 220 in fluid communication with the inflation lumen 201 of the monolithic single-layer distal outer member 230. The inflation lumen 201 of the monolithic single-layer distal outer member 230 depicted herein comprises a generally crescent configuration at a proximal section thereof and the hypotube 220 is inserted into the inflation lumen 201, as further discussed herein.

As embodied herein and as illustrated in FIG. 2, an exterior surface of the monolithic single-layer distal outer member 230 can define a proximal port 280. The proximal port 280 is spaced distally from the proximal end of the catheter 100. The proximal port 280 is configured to receive a guidewire 260 within the guidewire lumen 210 of the monolithic single-layer distal outer member 230 and inner tubular member 240. In some embodiments, the proximal port 280 is reinforced by the distal section of the hypotube 220 by disposing the distal section of the hypotube 220 proximate the proximal port 280 of the monolithic single-layer distal outer member 230. In some embodiments, at least a portion of the axial cut 440 is disposed proximate to the proximal port 280 of the guidewire lumen 210. The location of the proximal port 280 can depend upon various factors, such as the size of the balloon 140, as further discussed herein. In some embodiments, second angled cut 460 is proximal the proximal port 280, the axial cut 440 begins proximal the proximal port 280 and continues distal of the port 280 and first angled cut 420 is located distal of proximal port 280 and extends into a region where the monolithic single-layer distal outer member 230 and the inner tubular member are coaxial.

Figure 5:
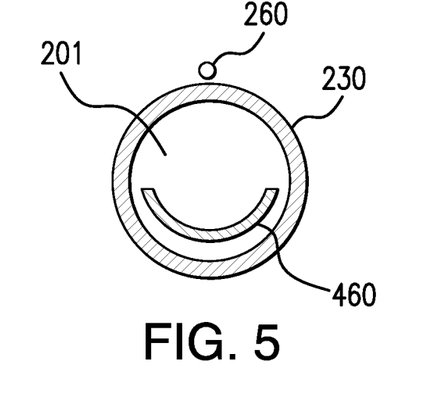

For purpose of illustration and not limitation, FIG. 4 is a cross-section of the catheter 100 of FIG. 2 along the lines 4-4. As depicted in FIG. 4, the hypotube 220 at this section is a single lumen member defining the inflation lumen 200 therethrough with a circular cross section. FIG. 5 is a cross-section of the catheter 100 of FIG. 2 along the lines 5-5. In FIG. 5, the inflation lumen 201 of the monolithic single-layer distal outer member 230 includes a substantially circular cross section. The inflation lumen 200 of the hypotube 220 is fluidly connected to the lumen 201 of the monolithic single-layer distal outer member 230. As depicted in FIG. 5, the second angled cut 460 is disposed within the inflation lumen 201 of the monolithic single-layer distal outer member 230, as further discussed herein.

Figure 6:
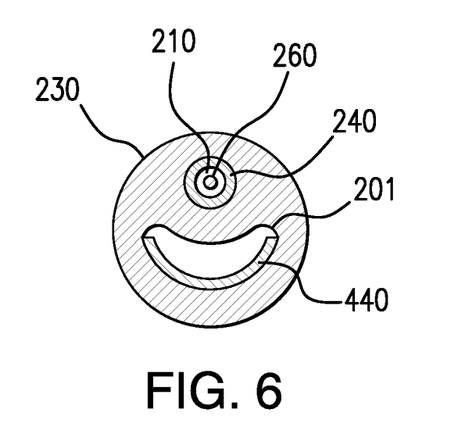

For purpose of illustration, FIG. 6 is a cross-section of the catheter 100 of FIG. 2 along the lines 6-6. The monolithic single-layer distal outer member 230 at 6-6 includes a crescent like cross section for the inflation lumen 201. With respect to FIGS. 5 and 6, the inflation lumen 201 of the monolithic single-layer distal outer member 230 transitions from a circular cross section at FIG. 5 to a crescent like cross section at FIG. 6. The transition of the circular cross section of the monolithic single-layer distal outer member 230 to the crescent like cross section of the monolithic single-layer distal outer member 230 allows for a smooth transition in flow, as described further herein. The crescent like cross section of inflation lumen 201 can provide for a catheter with a reduced profile as compared to a catheter having a round inflation lumen at locations proximate the proximal port 280.

As depicted in the cross section of FIG. 6, the axial cut 440 can be disposed at least partially in the crescent inflation lumen 201. The space around (e.g., above) the axial cut 440 can define the volume for inflation fluid flow. The corners of the crescent or "smiley" configuration can be rounded or otherwise provided in any suitable shape. The cross section also includes inner tubular member 240 and having guidewire lumen 210 and guidewire 260 disposed therein.

Figure 7:
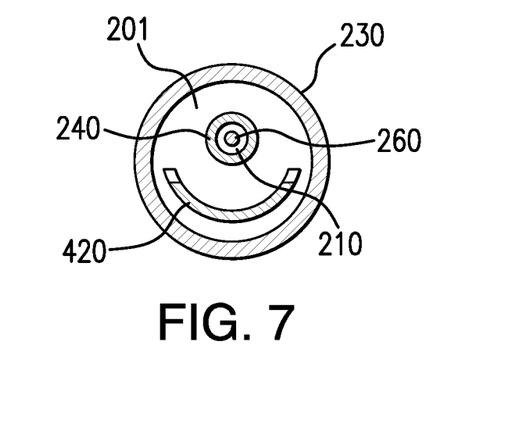

For purpose of illustration and not limitation, FIG. 7 is a cross-section of the catheter 100 of FIG. 2 along the lines 7-7. FIG. 7 depicts a cross section of the monolithic single-layer distal outer member 230 in which the inflation lumen 201 has transitioned from the crescent configuration to an annular configuration. The first angled cut 420 interfaces with the monolithic single-layer distal outer member 230 and is positioned adjacent and below, as depicted in FIG. 7, the guidewire lumen 210 as defined by inner tubular member 240 and having guidewire 260 disposed therein. The inflation lumen 201 is generally coaxial with the guidewire lumen 210.

Thus, as embodied herein and as shown in FIGS. 4-7, the inflation lumen 200 of the hypotube 220 transitions from a circular cross section at section 4-4 of FIG. 2, to a generally crescent or "smiley" configuration at section 6-6 of the inflation lumen 201 of the monolithic single-layer distal outer member 230 and then ultimately to an annular cross section at section 7-7 and 8-8. However, the inflation lumen 201 can have alternative cross-sectional shapes as desired.

In accordance with the disclosed subject matter, the skive can serve as a male end section of the hypotube 220 and the inflation lumen 201 of the monolithic single-layer distal outer member 230 can serve as the female receiving end section. At least a portion of the stepped skive at the distal end section of the hypotube 220 can be configured to be received within the inflation lumen 201 of the monolithic single-layer distal outer member 230. The skive of hypotube 220 can be disposed within the crescent or smiley shaped inflation lumen to fluidly connect the inflation lumen 200 of the hypotube 220 with the inflation lumen 201 of the monolithic single-layer distal outer member 230. For example, and as embodied herein the skive portion of the hypotube 220 is disposed within the inflation lumen 201 of the monolithic single-layer distal outer member 230, as depicted in FIGS. 1 and 6. The axial cut 440 can "float" within inflation lumen 201 and/or interface with a portion of a surface of the inflation lumen 201 of the monolithic single-layer distal outer member 230. In alternative embodiments, at least the axial cut 440 can be press fit with the inflation lumen 201 of the monolithic single-layer distal outer member 230. Furthermore, as embodied herein, the first angled cut 420 is inserted through the inflation lumen 201 of the monolithic single-layer distal outer member 230, as depicted in FIG. 2. Accordingly, the skive can assist in joining and reinforcing the hypotube 220 with the monolithic single-layer distal outer member 230, while facilitating a smooth transition in flexibility and reduce kinking of the catheter.

In accordance with the disclosed subject matter, the monolithic single-layer distal outer member 230 can be bonded to the hypotube 220. For example, the distal section of the hypotube 220 can have a roughened or textured outer surface to enhance the bond with the monolithic single-layer distal outer member 230. The hypotube 220 can be concentrically aligned within the monolithic single-layer distal outer member 230. Accordingly, the outer diameter or exterior surface of the hypotube 220 can be sized to fit concentrically within the interior surface of the monolithic single-layer distal outer member 230 at least at a distal section of the hypotube 220. The hypotube 220 can be bonded to the monolithic single-layer distal outer member 230 along the roughened or textured portion, with the remainder of the hypotube (e.g., including the skive) free of attachments to the monolithic single-layer distal outer member 230. Alternatively, in some embodiments, the hypotube 220 can be bonded with the monolithic single-layer distal outer member 230 along the length of the hypotube 220 or at portions along the length of the hypotube 220.

In some embodiments, the hypotube 220 can be free of any outer coating or jacket, so as to have a bare exposed outer surface. In this manner, a hypotube 220 of larger cross section can be provided without increasing the profile of the proximal shaft section 120 as compared to a conventional rapid exchange catheters with a coated or jacketed hypotube. For example, the reduction in thickness by omitting a coating can allow for a proportional increase in both the outer diameter and thus the inner diameter of the tubular member. Thus, the overall profile of the catheter along a proximal end section can remain the same, but the dimensions of the inflation lumen therein can be increased. The increase in inner diameter can result in greater fluid flow for increased inflation or deflation (e.g., decreased inflation and deflation times) as compared to conventional catheters. In some embodiments, a thicker hypotube can be provided that can provide increased strength and pushability without substantially effecting profile and or inflation time as compared to known jacketed hypotubes. Further, the bare hypotube can also result in a better grip and a reduction in kinking.

As embodied herein, the catheter shaft 110 includes a monolithic inner tubular member 240 that defines the guidewire lumen 210, 211 configured to slidably receive a guidewire 260 therein. As shown in FIG. 1 for illustration, the inner tubular member 240 can comprise one tube (i.e., monolithic and/or zero-transition) such that the inner tubular member 240 forms the tip 270. The zero-transition inner tubular member 240 can provide continuous flexibility, direct force transfer, crossing of challenging anatomy with less force, and tactile feedback.

Thus, from the proximal end section to the distal end section, the catheter 100 embodied herein transitions from a single lumen (inflation lumen) configuration in the proximal shaft section 120 to a coaxial dual lumen (inflation lumen and guidewire lumen) configuration in the distal shaft section 130. The area proximate the skive of hypotube 220 generally defines the juncture between the single lumen hypotube 220 and the coaxial dual lumen distal shaft section 130.

As depicted in FIG. 1, balloon 140 can be coupled to the monolithic single-layer distal outer member 230 and is in fluid communication with the inflation lumens 200, 201, and 202. For purpose of illustration and not limitation, FIG. 9 is a cross-section of the catheter 100 of FIG. 1 along the lines 9-9. As depicted in FIGS. 1 and 9, a balloon 140 is sealingly secured to the monolithic single-layer distal outer member 230 such that an interior of the balloon 140 is in fluid communication with inflation lumens 200, 201, and 202 and includes inner tubular member 240 and guidewire 260 therein. The balloon 140 is coupled to the monolithic single-layer distal outer member 230 by at least one of bonding, adhesive, lap joint, and butt joint or by other suitable configurations as known in the art, however, a lap joint formed via heat bonding is preferred.

Figure 12:
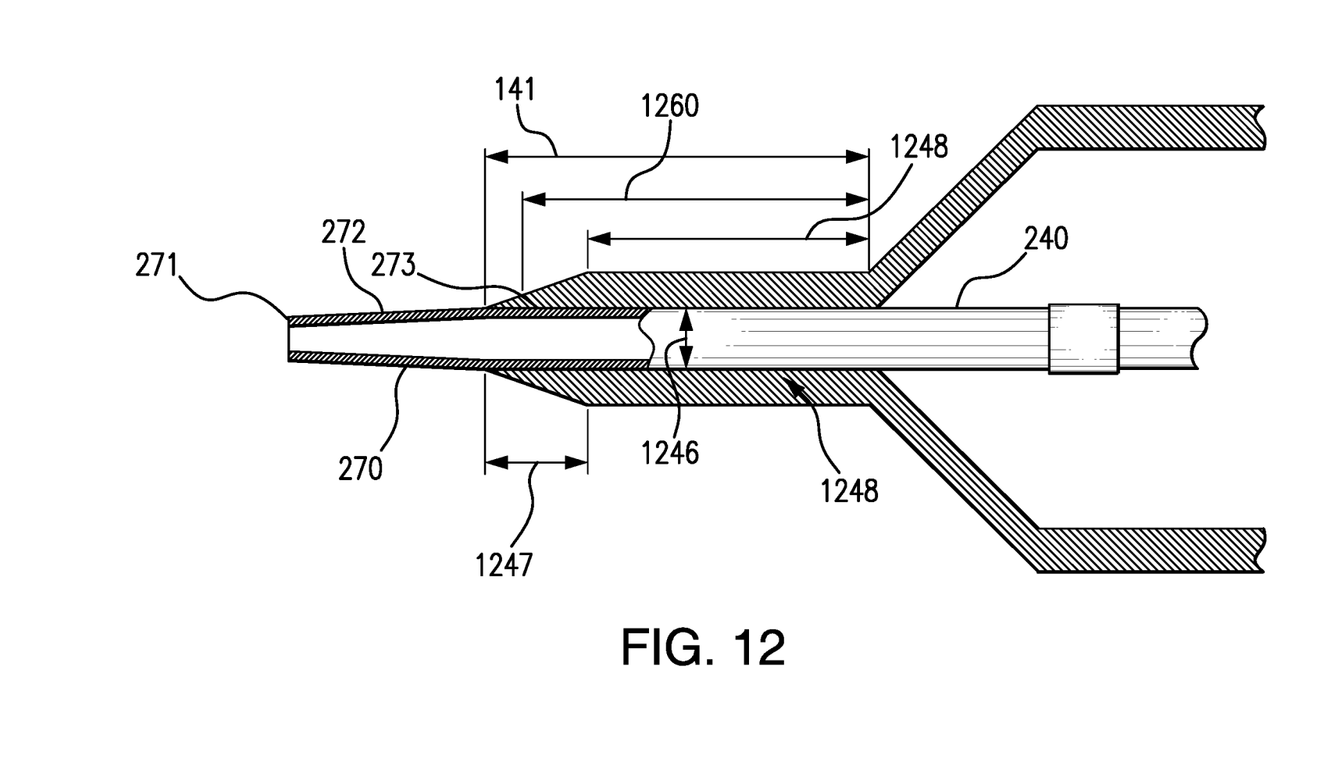
FIG. 12 is a partial side view of an inner tubular member and a balloon according to exemplary embodiments of the disclosed subject matter.

As shown in FIG. 1 for illustration and not limitation, the balloon 140 can have a proximal balloon shaft 145, a proximal cone portion 144, a proximal shoulder 147, a working length 143, a distal shoulder 146, a distal cone portion 142, and a distal balloon shaft 141. The balloon 140 can be coupled to the distal outer member 230 and monolithic inner tubular member 240 in any suitable manner. In some embodiments, the balloon 140 is coupled to the distal outer member 230 along a longitudinal length of the proximal balloon shaft 145 and coupled to the monolithic inner tubular member 240 along a longitudinal length of the distal balloon shaft 141, as depicted in FIG. 1. For example, the distal balloon shaft 141 can have a distal seal portion 1247 coupled to the monolithic inner tubular member 240 and a proximal portion 1248 of the distal balloon shaft free of attachment to the inner tubular member 240 as shown in FIG. 12 for the purpose of illustration and not limitation. The length of the proximal portion 1248 of the distal balloon shaft free of attachment can be at least about two times the inner diameter 1246 of the distal balloon shaft 141.

As embodied herein and shown in FIG. 12 for the purpose of illustration and not limitation, the inner tubular member 240 can be a monolithic piece that forms the tip 270 of the catheter. The tip 270 includes a distal exposed portion 272 and a proximal portion 273 along the length of the distal seal portion 1247 of the distal balloon shaft. In some embodiments, the length of the proximal portion 1248 of the distal balloon shaft is about 63% to about 67% the length of the tip 270. Furthermore, the length of the proximal portion 1248 of the distal balloon shaft can be about 30% to about 40% of the combined length of the distal balloon shaft 141 and the distal exposed portion 272 of the tip.

In some embodiments, the tip length 270 is less than about 5 mm (including the distal exposed portion 272 and the proximal portion 273). In some embodiments, the tip length can be about 3.0 mm to about 3.2 mm for 2.5 mm to 3.5 mm balloons. As discussed herein, the tip can taper distally and define a distal most tip 271 having an outer diameter of up to about 0.020 inches and inner diameter of about 0.015 inches minimum.

In some embodiments, the distal balloon shaft 141 can have inner and outer diameters that vary based on the size of the balloon: for 2.50 mm balloons, the inner diameter can be a minimum of 0.0220 inches and the outer diameter can be about 0.0290 inches; for 3.00 mm balloons, the inner diameter can be a minimum of 0.0220 inches and the outer diameter can be about 0.0325 inches; and for 3.5 mm balloons, the inner diameter can be a minimum of 0.0220 inches and the outer diameter can be about 0.0325 inches.

In some embodiments, the distal balloon shaft 141 can have a trim length 1260 prior to sealing to the inner tubular member 240 of about 2.8 mm to about 3.0 mm. The distal seal portion 1247 of the distal balloon shaft can have a length of about 1.2 mm. The proximal portion 1248 of the distal balloon shaft free of attachment to inner tubular member 240 can have a length of about 2.0 mm.

The balloon cone length can vary based on the size of the balloon. For example, for 2.5 mm to 3.00 mm diameter balloons (of any length), the balloon cone length can be about 3 mm. For 3.5 mm diameter (of any length), the balloon cone length can be about 4 mm.

Inner tubular member 240 including tip 270 and balloon 140 configurations in accordance with the disclosed subject matter unexpectedly provide for improved trackability, allowing the catheter to advance further within the vascular system of a patient. For example, the length of the proximal portion 1248 of the distal balloon shaft free of attachment to the inner tubular member 240 in accordance with the disclosed subject matter can provide for centering of the catheter (e.g., a coaxial position system) when traversing a bend in the vessel system, providing reduced stent damage as compared to known catheters due to contact with the side of the vessel (e.g., calcified lesions). Furthermore, known catheter systems having a distal balloon shaft entirely bonded to the inner tubular member and/or tip can have increased stiffness, which can reduce the trackability of the distal portion of the catheter as compared to catheters in accordance with the disclosed subject matter.

In accordance with the disclosed subject matter, the distal balloon shaft 141 of the balloon 140 can be coupled to the inner tubular member 240 in a plurality of suitable ways. For example, the distal balloon shaft 141 can be fusion bonded to the inner tubular member 240, for example, by applying heat to at least a portion of the area of overlap. For illustration and without limitation, electromagnetic energy, such as thermal, laser, or sonic energy can be applied to the distal balloon shaft 141 to bond at least a portion of the distal balloon shaft 141 to the inner tubular member 240. Heating the distal balloon shaft 141 can cause the polymeric material of the distal balloon shaft 141 to soften, or melt and flow, providing a distal seal portion 1247 with a tapered configuration as shown in FIG. 12.

In some embodiments, a heat shrink tubing (not shown) can be positioned around the outside of the distal balloon shaft 141, which can have a trim length of about 10 mm to about 15 mm prior to melt bonding. The heat shrink tubing, also referred to as a "heat shrink sleeve," can be composed of a polymeric material configured to shrink when exposed to heat. U.S. Pat. No. 7,951,259, which is hereby incorporated by reference in its entirety, discloses the use of a heat shrink sleeve in fabricating a catheter with a flexible distal end. The heat shrink tubing, when heated, shrinks and exerts an inward radial force on the distal balloon shaft 141. With the polymer of the distal balloon shaft 141 in a molten or softened state, the diameter of the distal balloon shaft 141 can be reduced by the force exerted by the heat shrink tubing. After the balloon 140 is cooled, the heat shrink tubing can be removed. Heating can be accomplished, for example, by laser heating (e.g., using a $CO_2$ laser), contact heating (e.g., using aluminum nitride, resistance, RF), hot air, resistance heating, induction heating or the like. As embodied herein, for purposes of illustration and not limitation, a solid state laser can be used to heat the shrink tubing and soften the distal balloon shaft 141. As a result, a portion of the outer surface of the distal balloon shaft 141, in its softened or molten state, can be bonded to the inner tubular member 240. Other catheter connections, such as the proximal balloon shaft 145 to the distal outer member 230 (e.g., via lap joint with proximal balloon shaft 145 over the distal outer member 230), can be formed using the fusion bonding methods described herein.

In some embodiments, the exposed portion 272 of the tip can be tapered or rounded as shown in FIG. 12 during the same laser bonding process as forming the bond between the distal balloon shaft 141 and the inner tubular member 240 by traversing the laser along the length of the tip 270 and allowing the molten material to flow distally. The tapered tip can provide improved maneuverability to traverse tortuous anatomy. The distal balloon shaft 141 provides an area to seal 1247 the distal end of the balloon 140 to the inner tubular member 240. In some embodiments, a smaller length of the seal can provide improved flexibility to the distal section of the catheter but still provide suitable tensile strength. A smaller length of the seal can also reduce heat-induced damage to the balloon cone during the heat bonding process (which could result in rupture) by increasing the distance between the location of the seal and the balloon cone section. According to some embodiments of the disclosed subject matter, the distal balloon shaft 141 can be non-milled. Forming the balloon 140 with a distal seal portion 1247 coupled to the inner tubular member 240 and a proximal portion 1248 free of attachment to the inner tubular member 240 according to the disclosed subject matter can improve catheter trackability through tortuous vasculature or the like.

As depicted in FIG. 1 for the purpose of illustration and not limitation, the balloon 140 can comprise as a single layer of polymer material. For example, the balloon 140 can comprise a wide variety of suitable polymer materials, for example, nylons, co-polyamides such as polyether block amides (for example commercially available as PEBAX®), polyester, co-polyester, polyurethane, polyethylene, or the like. The balloon 140 can be formed of a polymeric material which is compatible with the material forming the outer surface of the shaft, to allow for fusion bonding, although the balloon 140 can alternatively or additionally be adhesively bonded to the shaft. In some embodiments, the balloon 140 can comprise a single layer of polyether block amide (e.g., commercially available as PEBAX®). The polyether block amide can have any suitable Shore durometer hardness, such as between about 63D and 72D, for example about 72D.

Alternatively, multilayered balloons can be used. For example, the balloon 140 can have a first layer made of a first polymer material having a first Shore durometer hardness, and a second layer made of a second polymer having a second Shore durometer hardness. In some embodiments, the first Shore durometer hardness can be greater than the second Shore durometer hardness, and the first layer can be an outer layer relative to the second layer. For example, the balloon 140 can have a first outer layer of polyether block amide (e.g., commercially available as PEBAX®) having a Shore durometer hardness of between about 55D and about 63D and a second inner layer of polyether block amide having a Shore durometer hardness of between about 70D and about 72D. In some embodiments, the balloon 140 has a first outer layer of PEBAX® 72D and a second inner layer of PEBAX® 63D. Details of suitable multilayer balloons are described in U.S. Pat. No. 7,828,766, U.S. application Ser. No. 12/897,202, and U.S. application Ser. No. 13/680,299, the contents of each of which are herein incorporated by reference in their entirety.

In accordance with the disclosed subject matter, the balloon can have wings and be folded as known in the art. For example, the balloon can have three folds for 2.5 mm to 3.5 mm diameter balloons. The balloon folds can improve the uniformity of stent or scaffold deployment.

As embodied herein, the balloon 140 can be a relatively high rupture pressure, non-compliant balloon, which in some embodiments has a rupture pressure of about 20 atm to about 30 atm or more, such that the balloon 140 can be inflated in the patient during a procedure at relatively high working pressure of about 18 atm. The rated burst pressure of a catheter, calculated from the average rupture pressure, is the pressure at which 99.9% of the catheters can be pressurized to without rupturing, with 95% confidence. Generally, a balloon is inflated in the patient during a procedure at working pressure of about 8 atm to about 18 atm, preferably about 10 atm to about 18 atm. In some embodiments, the catheter with balloon 140 has a rated burst pressure of about 14 atm to about 25 atm. In embodiments having a single layer balloon 140 of PEBAX® 72D, the rated burst pressure can be at least about 16 atm. In embodiments having a balloon with a first outer layer of PEBAX® 72D and a second inner layer of PEBAX® 63D, the rated burst pressure can be about 18 atm and the nominal pressure can be about 10 atm. The balloon 140 can be any suitable size known in the art, e.g., 2.00, 2.25, 2.50, 2.75, 3.00, 3.25, 3.50, or 4.00 mm diameter.

Additional suitable materials, configurations, and methods of manufacture of the balloon 140 are provided in U.S. Pat. Nos. 7,074,206, and 8,052,638, the contents of each of which are hereby incorporated by reference in their entirety. Additional features proximate the balloon 140 can include markers (e.g., made of platinum/iridium and located both ends of the working length of the balloon), stents or scaffolds, and an atraumatic tip. Examples of such features and additional features include those described in U.S. Pat. No. 7,862,541; U.S. application Ser. No. 12/983,504; U.S. Pat. No. 7,549,975; U.S. application Ser. No. 12/468,745; U.S. Pat. No. 6,964,750; U.S. application Ser. No. 11/455,382; U.S. Pat. Nos. 7,833,597; 7,322,959; 7,303,798; U.S. application Ser. No. 11/775,480; U.S. application Ser. No. 12/945,566; U.S. Publication 2010/0285085; U.S. Publication No. 2010/0189876; U.S. Pat. No. 6,923,822; U.S. application Ser. No. 11/189,536; U.S. Publication No. 2009/0036829; U.S. Publication No. 2007/0021772; U.S. application Ser. No. 11/241,936; and U.S. application Ser. No. 14/212,966, the contents of each of which are herein incorporated by reference in their entirety.

In accordance with the disclose subject matter, the balloon 140 can have a stent or scaffold (not shown) mounted thereon for stent or scaffold delivery applications. The stent or scaffold can be made of any suitable material. For example, the scaffold can be bioresorbable and can be made of, for example, Poly(L-lactide) (PLLA). Alternatively, the stent can comprise a metal, e.g., a cobalt chromium alloy (e.g., L-605 comprising Co—Cr—W—Ni). For bioresorbable scaffolds, markers, e.g., comprising platinum, such as beads at the ends of the scaffold can be used, which can help in positioning the scaffold during delivery. The scaffold (or stent) can include one or more coatings, for example a bioresorbable coating, for example of Poly (D, L-lactide) (PDLLA) can be used.

The stent or scaffold can have any suitable dimensions (e.g., having a diameter of 2.5, 3.0, or 3.5 mm) and be any suitable length, e.g., 8, 12, 15, 18, 23, or 28 mm. The stent or scaffold can have any suitable configuration as known in the art. The inner tubular member can include markers along its longitudinal length. For example, the inner tubular member can have a distal marker 148 and a proximal marker 149 along its length, as shown in FIG. 1. In some embodiments, the middle of the markers are longitudinally aligned with the ends of stent or scaffold to improve placement of the stent or scaffold at the target site during treatment. The markers can be about 1.0 mm wide for 8 mm to 28 mm stents or scaffolds. The shaft (e.g., the hypotube) can also include proximal markers 95 cm and 105 cm proximal of the distal tip.

As embodied herein, the stent or scaffold can include a drug and/or or polymer coating as known in the art.

As depicted in FIG. 1 for purpose of illustration and not limitation, an adapter 225 (e.g., single arm) and a strain relief can be provided at the proximal end of the catheter 100 for access to the inflation lumens 200, 201, 202 collectively, and can be configured for connecting to an inflation fluid source (not shown). The balloon 140 can be provided at a distal end of the catheter and in fluid communication with the inflation lumens 200, 201, 202. The distal end of the catheter can be advanced to a desired region of a body lumen in a conventional manner and balloon 140 inflated to perform a medical procedure, such as to dilate a stenosis and/or deliver a stent, scaffold, or the like. The catheter 100 is then withdrawn or repositioned for another procedure. FIG. 1 illustrates the balloon 140 in an inflated configuration.

In accordance with the disclosed subject matter, the catheter components can comprise a variety of suitable materials. For example, the hypotube 220 can be a more rigid material than the material of the distal outer member 230. In some embodiments, the hypotube 220 can be a relatively high stiffness material including a metal, such as but not limited to stainless steel (e.g., 304), although a high durometer polymer can be used. The distal outer member 230, coupled to the hypotube 220, can be more flexible than the hypotube 220 and can comprise a more flexible material. In some embodiments, the distal outer member 230 can be a single layer and can comprise a polyether block amide (e.g., commercially available as PEBAX®) having as shore Durometer hardness of about 72D. Alternatively, the distal outer member 230 can comprise other polymers and/or can be a multilayer member made of one or more polymers, such as different Shore durometer hardness of polyamide or polyether block amides.

As embodied herein, the monolithic inner tubular member 240 can be a single layer or multilayer member made of one or more polymeric materials. For example, the inner tubular member 240 can comprise outer, inner and intermediate layers. The layers can be made of any suitable materials. For example, the outer layer can comprise a polyether block amide and/or nylon, the inner layer can comprise a lubricious polymer, and the intermediate layer can comprise a tie layer to bond the outer layer and the inner layer. In some embodiments, the outer layer comprises a polyether block amide, the inner layer comprises high density polyethylene (HDPE), and the intermediate layer comprises an ethylene acrylic acid adhesive polymer commercially available as Primacor®. The inner tubular member 240 can have any suitable dimensions, such as an outer diameter of about 0.0200 inches to about 0.0225 inches and an inner diameter of about 0.016 inches to about 0.0165 inches.

In accordance with the disclosed subject matter, a rapid exchange proximal port 280 can be formed in the distal outer member 230 at any suitable location along the length of the catheter using any technique known in the art. For example, an opening can be formed in the side wall of the distal outer member 230 and the inner tubular member 240 can be inserted through the opening to extend distally within the catheter (e.g., through the distal outer member and balloon). A mandrel or pressurizing fluid can be provided within the guidewire lumen 210 of the inner tubular member 240 to maintain the round shape of the guidewire lumen 210 during bonding, and optionally a shrink wrap can be provided over the distal outer member 230 proximate the opening. The distal outer member 230 can be fusion bonded, for example by heating with a laser, to the inner tubular member 240 within the interior of the distal outer member 230. The crescent shape of the inflation lumen 201, as shown in FIG. 10B for illustration, of the distal outer member 230 can be formed during the heating process by positioning a crescent shaped mandrel within the distal outer member 230 proximate the port. The heating process can provide a temperature sufficient to soften or melt the materials of the distal outer member 230 and the inner tubular member 240 to define the lumens therein. Shrink wrap material can be used to maintain the outer shape and dimension of the distal outer member 230 by the fusion process. The mandrel and shrink wrap can then be removed after the fusion or heating process is complete.

Figure 10A:
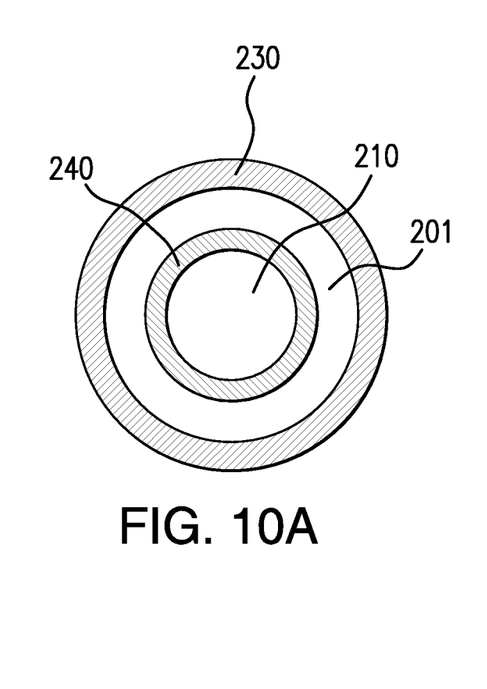
FIGS. 10A and 10B are schematic views of the cross section of the distal shaft section according to embodiments the disclosed subject matter.
Figure 10B:
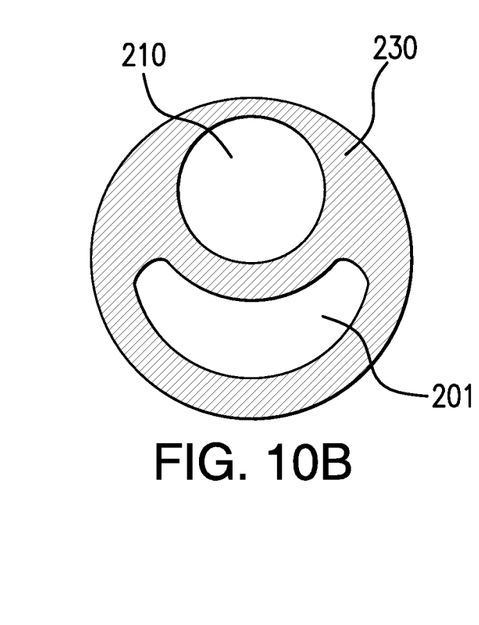

For purpose of illustration and not limitation, FIGS. 10A and 10B depict cross-sections of the distal outer member 230 during manufacture. FIG. 10A depicts the cross section of the distal outer member 230 and inner tubular member 240 of a coaxial configuration, where the guidewire lumen 210 is concentric with the inflation lumen 201, similar to FIG. 8. FIG. 10B depicts a cross-section from the distal outer member 230 after the melting or fusion process depicting the inflation lumen 201 defined by a crescent mandrel. The dual lumen configuration of FIG. 10B can be formed as described above or by alternative techniques known in the art. For example, the distal outer member 230 can be molded to include a dual lumen member extending at least a length thereof for purpose of strength and transition from the proximal end section to the distal end section.

As embodied herein, after necking as described above, the catheter can be subsequently assembled, at least by sealingly securing a balloon 140 to a distal end of the distal outer member 230 via heat bonding, as described herein, such that the balloon 140 has an interior in fluid communication with the inflation lumen 202 of the distal outer member 230. Portions of the catheter can be coated as known in the art, for example with a hydrophilic coating of poly(ethylene oxide) (PEO).

Catheters in accordance with the disclosed subject matter can be of any suitable dimensions, but preferably the shaft can have a reduced profile. For example, the proximal portion of the shaft can have a maximum diameter of about 0.0480 inches, and the distal outer member can have a diameter of 0.037 inches to about 0.040 inches. The crossing profile can be about 0.060 inches (for a 3.0×18 mm balloon) and the tip entry profile can be about 0.021 inches. The working length of the catheter can be about 145 cm.

Example 1

The burst pressure of balloon catheters having various sized balloons prepared in accordance with the disclosed subject matter were tested in accordance with ISO10555-4: 2013, and the results are shown in Table 1. The balloon catheters included a monolithic single-layer distal outer member 230 comprising PEBAX® 72D necked along its entire length and a hypotube comprising a skive defined by a first angled cut, an axial cut, and a second angled cut as described herein above. As demonstrated by the data in Table 1, balloon catheters in accordance with the disclosed subject matter provide burst pressures significantly above the acceptance criteria (i.e., 16 atm), which is used for typical inflation pressures in medical procedures. For example, for 2.5 mm, 3.0 mm, and 3.5 mm diameter balloons, the average burst pressure was 41 atm, 44 atm, and 41 atm, respectively.

TABLE 1

| Balloon Size (diameter × length) | Quantity Tested | Avg. BP | Standard Deviation | Min BP | Max BP |
| --- | --- | --- | --- | --- | --- |
| 2.5 mm × 28 mm | 17 | 41 | 0.8 | 40 | 42 |
| 2.5 mm × 28 mm | 17 | 44 | 0.0 | 44 | 44 |
| 2.5 mm × 28 mm | 16 | 41 | 0.7 | 10 | 42 |

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of making a balloon catheter, comprising:
necking a tubular member of polymer material to form a monolithic single-layer distal outer member necked along an entire length thereof with the polymer material consisting essentially of polymer chains in a linear orientation;
providing a hypotube;
coupling a proximal end of the monolithic single-layer distal outer member to the hypotube to form an outer shaft having an inflation lumen defined therethrough;
providing a balloon in fluid communication with the inflation lumen, the balloon having a distal balloon shaft, a distal cone portion, a distal shoulder, a working length, a proximal shoulder, a proximal cone portion, and a proximal balloon shaft;
coupling the proximal balloon shaft to a distal end of the monolithic single-layer distal outer member; and
providing a monolithic inner tubular member having a guidewire lumen defined therethrough, the monolithic inner tubular member extending distally from a proximal port in the monolithic single-layer distal outer member through the balloon to form a tip.

2. The method of claim 1, wherein the balloon further comprises a distal balloon shaft having an inner diameter, and further comprising coupling a distal seal portion of the distal balloon shaft to the monolithic inner tubular member and allowing a proximal portion of the distal balloon shaft to be free of attachment to the monolithic inner tubular member.

3. The method of claim 2, wherein the length of the proximal portion of the distal balloon shaft is at least two times the inner diameter of the distal balloon shaft.

4. The method of claim 1, wherein the tubular member is necked from a first outer diameter of 0.045 inches to a first reduced outer diameter of 0.038 inches to 0.039 inches and from a first inner diameter of 0.033 inches to a first reduced inner diameter of 0.029 inches to 0.0295 inches along a proximal portion of the monolithic single-layer distal outer member.

5. The method of claim 1, wherein the tubular member is necked from a first outer diameter of 0.045 inches to a second reduced outer diameter of 0.034 inches to 0.035 inches and from a first inner diameter of 0.033 inches to a second reduced inner diameter of 0.029 inches to 0.0295 inches along the distal end of the monolithic single-layer distal outer member.

6. The method of claim 1, wherein the length of the distal end of the monolithic single-layer distal outer member is 1.0 mm to 1.2 mm.

7. The method of claim 1, further comprising mounting a bioresorbable scaffold on the balloon.

8. The method of claim 1, wherein the monolithic single-layer distal outer member has a double wall thickness of 0.0085 inches to 0.01 inches.

* * * * *